US011426415B2

(12) United States Patent
Urano et al.

(10) Patent No.: US 11,426,415 B2
(45) Date of Patent: Aug. 30, 2022

(54) TREATMENT FOR WOLFRAM SYNDROME AND OTHER ENDOPLASMIC RETICULUM STRESS DISORDERS

(71) Applicants: Washington University, St. Louis, MO (US); The United States of America, As Represented by the Secretary, Department of Health and Human Services, Office of Technology Transfer, National Institutes of Health, Bethesda, MD (US)

(72) Inventors: Fumihiko Urano, St. Louis, MO (US); Jana Mahadevan, Temecula, CA (US); Amy Clark, St. Louis, MO (US); Ajit Jadhav, Chantilly, VA (US); David Maloney, Point of Rocks, MD (US); Brandon Harvey, Parkville, MD (US); Shyh-ming Yang, Doylestown, PA (US); Mark Henderson, Damascus, MD (US)

(73) Assignees: Washington University, St. Louis, MO (US); The United States of America, As Represented by the Secretary, Department of Health and Human Services, Bethesda, MD (US)

( * ) Notice: Subject to any disclaimer, the term of this patent is extended or adjusted under 35 U.S.C. 154(b) by 95 days.

(21) Appl. No.: 16/491,826

(22) PCT Filed: Mar. 6, 2018

(86) PCT No.: PCT/US2018/021167
§ 371 (c)(1),
(2) Date: Sep. 6, 2019

(87) PCT Pub. No.: WO2018/165171
PCT Pub. Date: Sep. 13, 2018

(65) Prior Publication Data
US 2021/0128580 A1    May 6, 2021

Related U.S. Application Data

(60) Provisional application No. 62/467,632, filed on Mar. 6, 2017.

(51) Int. Cl.
*A61K 31/554* (2006.01)
*A61K 9/00* (2006.01)
*A61K 31/155* (2006.01)
*A61K 31/4178* (2006.01)
*A61K 31/4985* (2006.01)
*A61K 45/06* (2006.01)
*C07K 14/605* (2006.01)

(52) U.S. Cl.
CPC .......... *A61K 31/554* (2013.01); *A61K 9/0019* (2013.01); *A61K 31/155* (2013.01); *A61K 31/4178* (2013.01); *A61K 31/4985* (2013.01); *A61K 45/06* (2013.01); *C07K 14/605* (2013.01)

(58) Field of Classification Search
CPC ........................... A61K 31/554; A61K 31/155
See application file for complete search history.

(56) References Cited

U.S. PATENT DOCUMENTS

| 5,416,066 | A    | 5/1995  | Kaneko et al. |
| 7,393,652 | B2   | 7/2008  | Marks |
| 7,544,678 | B2   | 6/2009  | Marks et al. |
| 8,022,058 | B2   | 9/2011  | Marks et al. |
| 8,710,045 | B2 * | 4/2014  | Marks ................. A61P 9/06 514/211.05 |
| 10,441,574 | B2 * | 10/2019 | Urano ............... A61K 31/4178 |
| 10,751,387 | B2 * | 8/2020  | Sun ..................... A61K 31/395 |
| 2011/0172190 | A1 | 7/2011  | Marks et al. |
| 2014/0088171 | A1 | 3/2014  | Yan et al. |
| 2014/0135313 | A1 | 5/2014  | Kaneko et al. |

FOREIGN PATENT DOCUMENTS

| EP | 2163248 B1 | 8/2012 |
| WO | 2008060332 A2 | 5/2008 |
| WO | 2010114562 A1 | 10/2010 |
| WO | 2010114563 A1 | 10/2010 |
| WO | 2016077706 A1 | 5/2016 |
| WO | WO-2016077706 A1 * | 5/2016 ........... A61K 9/0019 |

OTHER PUBLICATIONS

Back et al., "Endoplasmic Reticulum Stress in the Beta-Cell pathogenesis of Type 2 Diabetes", 2012, Experimental Diabetes Research, 11 pages.
Bellinger et al., "Remodeling of Ryanodine Receptor Complex Causes "Leaky" Channels: A Molecular Mechanism for Decreased Exercise Capacity," 2008, PNAS, 105(6): 2198-2202, 5 pages.
Eefting, F., et al., "Role of Apoptosis in Reperfusion Injury," 2004, Cardiovascular Research, 61:414-426, 13 pages.
Hara, T., et al., "Calcium Efflux from the Endoplasmic Reticulum Leads to Beta Cell Death," 2013, Endocrinology, Downloaded from press.endocrine.org, Feb. 20, 2014, 12 pages.
Hunt, D.J., et al., "K201 (JTV519) Suppresses Spontaneous Ca2+ Release and [3H]Ryanodine Binding to RyT2 Irrespective of FKBP 12.6 Association," 2007, Biochem J, 404: 431-438, 8 pages.
James, A.F., "Inhibition of SR CA2+ Uptake: A Novel Action of the RyR2-FKBP12.6 antagonist K201," Cardiovascular Research, 76:199-201, 3 pages.
Kaneko, N., "New 1,4-Benzothiazepine Derivative, K201, Demonstrates Cardioprotective Effects Against Sudden Cardiac Cell Death and Intracellular Calcium Blocking Action," Research Article, 1994 Wiley-Liss, Inc., 10 pages.

(Continued)

*Primary Examiner* — Kevin E Weddington
(74) *Attorney, Agent, or Firm* — Stinson LLP (57) ABSTRACT

The present invention generally relates to compositions and methods for treating or preventing an endoplasmic reticulum stress disorder in subjects, including compositions and methods for treating or preventing Wolfram syndrome. The present invention also relates to methods for treating symptoms of neurodegenerative diseases.

11 Claims, 10 Drawing Sheets

(56) References Cited

OTHER PUBLICATIONS

Kehat, I., "Novel Strategies for the Treatment of Heart Failure," 2012, Rambam Maimonides Med J, 3/2:e0011, 10 pages.

Kohno, M., et al., "A new cardioprotective agent, JTV519, Improves Defective Channel Gating of Ryanodine Receptor in Heart Failure," 2003, Am J Phsiol Heart Circ Physiol, 284:H1035H1042, 8 pages.

Kushnir, A., et al., "Ryanodine Receptor Patents," 2012, Recent Pat Biotechnol, 6/3:157-166, 18 pages.

Lu, S., et al., "A Calcium-Dependent Protease as a Potential Therapeutic Target for Wolfram Syndrome," 2014, PNAS, 111(49) E5292-E5301 www.press.org/cgi/boi/10.1073/pnas, 16 pages.

Lu, S., "Calcium Dependent Regulatory Mechanism in Wolfram Syndrome: A Dissertation," 2015, University of Massachusetts Medical School, GSBS Dissertations and Theses, Paper 773, http://escholarship.umassmed.edu/gsbs_diss/733, 117 pages.

Mekahli, D., et al., "Endoplasmic-Reticulum Calcium Depletion and Disease," 2011, Cold Spring Harb Perspect Biol, 3:a004317/1-30, 30 pages.

Pei, Y., et al., "Efficient Syntheses of Benzothiazepines as Antagonists for the Mitochondrial Sodium-Calcium Exchanger: Potential Therapeutics for Type II Diabetes," 2003, J Org Chem, 68(1):92-103, 12 pages.

Sedej, S., et al., "Subclinical Abnormalities in Sarcoplasmic Reticulum Ca2+ Release Promote Eccentric Myocardial Remodeling and Pump Failure Death in Response to Pressure Overload," 2014, J Am Coll Card, 63(15): 1569-1579, 11 pages.

Turan, B., et al., "Ryanodine Receptor: A New Therapeutic Target to Control Diabetic Cardiomyopathy", 2011, Antioxidants & Redox Signaling, 15/7:1847-1861, Abstract Only, 1 page.

International Preliminary Report on Patentability issued in PCT/US2018/021167, dated Sep. 19, 2019, 7 pages.

International Search Report and Written Opinion issued in PCT/US2018/021167, dated May 10, 2018, 12 pages.

\* cited by examiner

TREATMENT FOR WOLFRAM SYNDROME AND OTHER ENDOPLASMIC RETICULUM STRESS DISORDERS

REFERENCE TO RELATED APPLICATIONS

This application is the 371 National Stage Application of International Application Serial No. PCT/US2018/021167, filed Mar. 6, 2018, and claims the benefit of U.S. Provisional Application Ser. No. 62/467,632, filed Mar. 6, 2017, the contents of which are incorporated by reference herein.

GOVERNMENT LICENSE RIGHTS

This invention was made with government support under DK067493 and TR002065 awarded by the U.S. National Institutes of Health. The government has certain rights in the invention.

FIELD OF THE INVENTION

The present invention generally relates to compositions and methods for treating or preventing an endoplasmic reticulum stress disorder in subjects, including compositions and methods for treating or preventing Wolfram syndrome. The present invention also relates to methods for treating symptoms of neurodegenerative diseases.

BACKGROUND OF THE INVENTION

Wolfram syndrome is a rare autosomal recessive disorder characterized by diabetes insipidus, diabetes mellitus, optic atrophy, and deafness (also known as DIDMOAD). Insulin dependent diabetes usually occurs as the initial manifestation during the first decade of life, while the diagnosis of Wolfram syndrome is invariably later with onset of the other features in the second and ensuing decades. Two causative genes for this genetic disorder have been identified and are named WFS1 and WFS2. It has been shown that multiple mutations in the WFS1 gene, as well as a specific mutation in the WFS2 gene, lead to β cell death and neurodegeneration through endoplasmic reticulum (ER) and mitochondrial dysfunction. WFS1 gene variants are also associated with a risk of Type 2 diabetes and Type 1 diabetes. Moreover, a specific WFS1 variant can cause autosomal dominant diabetes.

Wolfram syndrome is caused by stress in the ER, a cell component involved in many vital functions of the eyes, brain, and pancreas. The ER is a membrane-bound organelle that is crucial for the folding and maturation of proteins, lipid biosynthesis, and homeostasis of intracellular $Ca^{2+}$ and reduction-oxidation (redox) potential. Protein folding and modification in the ER is highly sensitive to disturbances of ER homeostasis, including altered glycosylation, ER $Ca^{2+}$ depletion, increased mRNA translation, oxidative stress, energy deprivation, metabolic challenge, and inflammatory stimuli. The accumulation of unfolded and misfolded proteins in the ER lumen, termed ER stress, activates intracellular signaling pathways to resolve the protein folding defect. This unfolded protein response (UPR) increases the capacity of ER protein folding and modification, reduces global protein synthesis, and activates ER-associated protein degradation (ERAD). If ER stress is too severe or chronic, or the UPR is compromised and not able to restore the protein folding homeostasis, then numerous apoptotic signaling pathways are activated.

Calpain-2 protease has been found to provide a link between the ER and death of neurons and β cells in Wolfram syndrome. See WO2016/077706 A1, which is hereby incorporated herein by reference. Evidence indicates that ER dysfunction triggers a range of human chronic diseases, including Type 1 and Type 2 diabetes, atherosclerosis, inflammatory bowel disease, retinitis pigmentosa, congenital deafness, idiopathic nephrotic syndrome, and neurodegenerative diseases, such as amyotrophic lateral sclerosis (ALS), Parkinson's disease, and Alzheimer's disease. Thus, there remains a need for effective therapies targeting the ER for treating Wolfram syndrome and other ER stress disorders.

SUMMARY OF THE INVENTION

Briefly, various aspects of the present invention are directed to methods for treating or preventing an endoplasmic reticulum (ER) stress disorder in a subject in need thereof. The methods comprise administering to the subject a pharmaceutical composition comprising a therapeutically effective amount of at least one compound selected from the group consisting of JTV519, oxidized JTV519, salts and esters thereof, and mixtures thereof. In further aspects, the present invention is directed to methods for treating or preventing clinical symptoms of an ER stress disorder, such as Wolfram syndrome, in a subject in need thereof comprising administering to the subject a pharmaceutical composition comprising a therapeutically effective amount of at least one compound selected from the group consisting of JTV519, oxidized JTV519, salts and esters thereof, and mixtures thereof.

In other aspects, the present invention is directed to methods for treating motor dysfunction (e.g., improving motor function) in a subject in need thereof suffering from a neurodegenerative disease comprising administering to the subject a pharmaceutical composition comprising a therapeutically effective amount of at least one compound selected from the group consisting of JTV519, oxidized JTV519, salts and esters thereof, and mixtures thereof.

Still further aspects of the present invention are directed to various pharmaceutical compositions comprising a therapeutically effective amount of at least one compound selected from the group consisting of JTV519, oxidized JTV519, salts and esters thereof, and mixtures thereof and at least one additional active agent (e.g., dantrolene, azumolene, or pharmaceutically acceptable salts or hydrates thereof).

Other objects and features will be in part apparent and in part pointed out hereinafter.

DETAILED DESCRIPTION OF THE INVENTION

In various aspects, the present invention is directed to methods for treating or preventing an endoplasmic reticulum (ER) stress disorder in a subject in need thereof. The methods comprise administering to the subject a pharmaceutical composition comprising a therapeutically effective amount of at least one compound selected from the group consisting of JTV519, an oxidized form of JTV519 (referred to as oxidized JTV519 herein), salts and esters thereof, and mixtures thereof. The present invention is also directed to methods for treating or preventing clinical symptoms of an ER stress disorder, such as Wolfram syndrome, in a subject in need thereof comprising administering to the subject a pharmaceutical composition comprising a therapeutically effective amount of at least one compound selected from the group consisting of JTV519, oxidized JTV519, salts and esters thereof, and mixtures thereof. Clinical symptoms can include, for example, β cell and neuronal cell death. The present invention is further directed to methods for treating motor dysfunction (e.g., improving motor function) in a subject in need thereof suffering from a neurodegenerative disease comprising administering to the subject a pharmaceutical composition comprising a therapeutically effective amount of at least one compound selected from the group consisting of JTV519, oxidized JTV519, salts and esters thereof, and mixtures thereof.

Figure 1A:
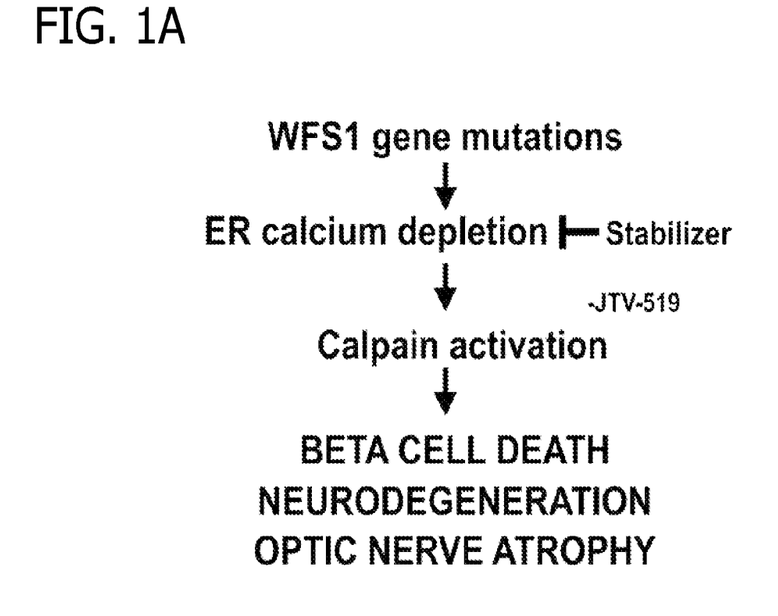
FIG. 1 is a depiction of the pathogenesis of Wolfram syndrome and target of JTV519.
Figure 1B:
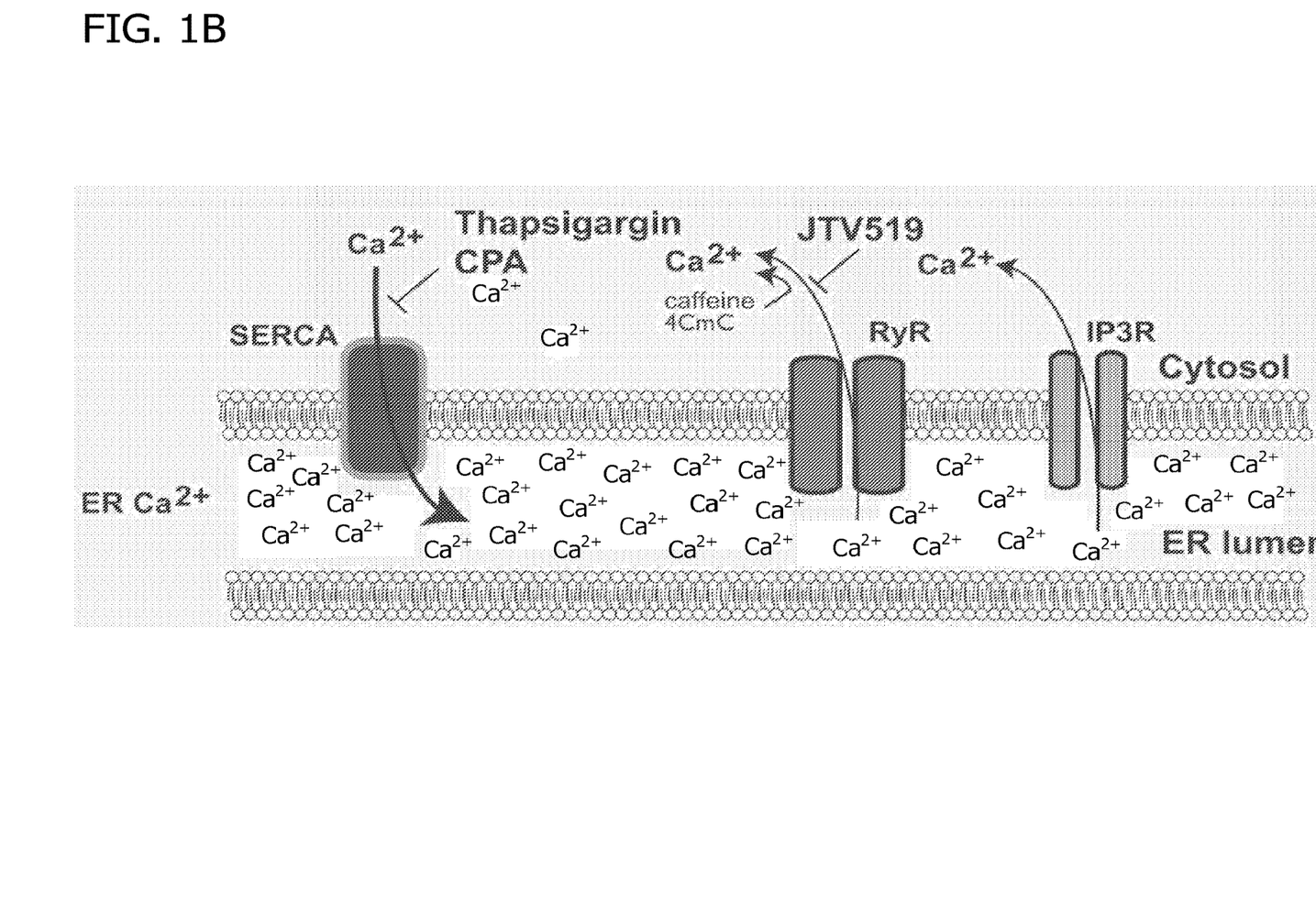

Although Wolfram syndrome is a rare disease and is currently neglected from mainstay drug discovery efforts, the homogeneity of the subject population and disease mechanism has enabled identification of an important drug target, a calcium-dependent protease, calpain-2. Calpain-2 hyperactivation is seen in both cell models and mouse models of Wolfram syndrome. Without being bound by theory, FIG. 1 (A and B) presents a proposed explanation for the pathogenesis of Wolfram syndrome and the target of JTV519 and/or oxidized JTV519. ER calcium homeostasis is regulated by sarco-endoplasmic reticulum Ca$^{2+}$ ATPase (SERCA) pump, ryanodine receptors (RyR), and inositol triphosphate receptors (IP3R) localized to the ER. SERCA maintains a high concentration of calcium in the ER and keeps a steep calcium gradient between the cytosol and ER. The calcium efflux from the ER is controlled by RyR and IP3R. Mutant leaky ryanodine receptor 2 (RyR2) causes ER calcium leakage to the cytosol, ER stress in β cells, and β cell dysfunction in humans and mice.

It has been discovered that JTV519 and oxidized JTV519 can prevent the leakage of ER calcium to the cytosol and abnormal activation of the pro-apoptotic enzyme, calpain-2, in models of Wolfram syndrome. JTV519 and oxidized JTV519 can prevent cell death in β cell models of Wolfram syndrome. Without being bound by theory, it is believed that JTV519 and oxidized JTV519 potentially suppress ER calcium leakage through RyR2 modulation and that these compound act on RyR2 in its closed states and prevent ER calcium leakage. This discovery provides for methods for treating and preventing endoplasmic reticulum stress disorders, including Wolfram syndrome.

The chemical structures of JTV519 and its oxidized analog are shown below:

JTV519: X = S
Oxidized JTV519: X = SO

JTV519 and its synthesis are described in U.S. Pat. No. 5,416,066. JTV519 is also known as K201 and by the chemical name 3-(4-benzyl-1-piperidinyl)-1-(7-methoxy-2, 3-dihydro-1,4-benzothiazepin-4(5H)-yl)-1-propanone. The oxidized analog of JTV519 (oxidized JTV519) and its synthesis is described in U.S. Patent Application Publication No. 2014/0135313. These patent documents are hereby incorporated herein by reference. Salts of these compounds include, for example, the HCl salt. Esters of these compounds include, for example, the fumarate and hemifumarate esters.

Even though Wolfram syndrome is an autosomal recessive and rare genetic disorder rooted in mutations in the WFS1 gene, it is a prototype of ER stress disorder and has relevance to Type 1 and Type 2 diabetes, retinal degeneration, and neurodegeneration (e.g., neurodegenerative diseases). The first clinical manifestation of Wolfram syndrome is juvenile-onset diabetes mellitus, which results from ER stress-mediated β cell dysfunction and death. Single-nucleotide polymorphisms (SNPs) in the WFS1 gene have been linked to Type 1 diabetes and Type 2 diabetes. Three missense mutations in the WFS1 gene have been identified as non-autoimmune genetic causes of Type 1 diabetes. This result is consistent with histopathology reports of Wolfram syndrome patients, who also exhibit β cell loss and early-onset diabetes, but no autoimmune markers. Association studies for Type 2 diabetes have also identified WFS1 gene polymorphisms that protect or predispose to the disease. Previous reports indicate that WFS1 plays a role in insulin production and β cell survival. Therefore, WFS1 is a locus of broad interest to the field of diabetes, particularly as a genetic model of how ER dysfunction, specifically ER stress, contributes to human disease, especially β cell death in diabetes. Evidence also indicates that ER stress-mediated cell death plays a critical role in the pathogenesis of retinal degeneration and neurodegeneration, which are major manifestations of Wolfram syndrome.

Accordingly, various aspects of the present invention are directed to methods for treating or preventing not only Wolfram syndrome but also other ER stress disorders including Type 1 and Type 2 diabetes, atherosclerosis, inflammatory bowel disease, retinitis pigmentosa, congenital deafness, idiopathic nephrotic syndrome, and neurodegenerative diseases. Specific neurodegenerative diseases include, for example, amyotrophic lateral sclerosis (ALS), Parkinson's disease, Alzheimer's disease, Huntington's disease, prion diseases, and/or spinocerebellar ataxias. As noted, various methods of the present invention are also directed to treating motor dysfunction (e.g., improving motor function) in a subject in need thereof suffering from a neurodegenerative disease comprising administering to the subject a pharmaceutical composition comprising a therapeutically effective amount of at least one compound selected from the group consisting of JTV519, oxidized JTV519, salts and esters thereof, and mixtures thereof.

Many neurodegenerative diseases are caused or strongly linked to misfolded protein species that accumulate in the ER or in the cytosol and trigger ER stress responses that ultimately lead to apoptosis. Also, altered calcium homeostasis has been associated with neurodegenerative diseases. See, for example, Doyle et al., Journal of Cellular and Molecular Medicine, 2011, 15(10):2025-2039; Bezprozvanny, Acta Naturae 2010, 2(4): 72-80; Leal et al., 2015 Frontiers in Cellular Neuroscience 2015, 9:225; and Chan et al., Journal of Neuroscience 2009, 28:12713-12724. Therefore, reducing or inhibiting the release of $Ca^{2+}$ from the ER can directly mitigate this stress response and help prevent neuronal death.

Alzheimer's disease (AD) is characterized by progressive dementia caused by neurodegeneration linked to Aβ plaques and intracellular hyper-phosphorylated tau inclusions. Various genetic mutations linked to AD seem to contribute to these pathologies which in turn directly affect calcium homeostasis in the ER and exacerbate ER stress. For instance, Aβ has been shown to trigger excessive $Ca^{2+}$ release from the ER. In addition, mutations in presenilins lead to the formation of new ER calcium channels and the upregulation of the native calcium channels, IP3R and RyR (Bezprozvanny, 2010; Doyle et al., 2011). Therefore, treatments and therapies that restore ER calcium homeostasis by inhibiting these ER calcium channels can treat the symptoms of AD, particularly motor dysfunction.

Parkinson's disease (PD) is characterized by motor symptoms such as dyskinesia, muscle rigidity, postural instability and resting tremor. It is caused by the degeneration of the dopaminergic neurons of the nigrostriatal pathway and is associated with the accumulation of a misfolded protein species, α-synuclein, into intracellular inclusions called Lewy bodies. Dopaminergic neurons, due to their intrinsic activity, are particularly prone to disruptions in calcium homeostasis (Chan et al., 2009). Evidence suggests that elevated ER stress contributes to the degeneration of these neurons in this disease (Doyle et al., 2011). Therefore, reducing $Ca^{2+}$ flux can be a tractable means to delay the onset of PD symptoms (e.g., motor dysfunction) or slow its progression (Chan et al., 2009).

Amyotrophic lateral sclerosis (ALS) is a progressive fatal neurodegenerative disease that principally affects motor neurons. It has been linked to a variety of misfolded or mutated proteins including SOD1. There is evidence that these mutated proteins lead to elevated calcium influx into the cell, which in turn overwhelms mitochondria tasked with clearing it, disrupting the ER mitochondrial calcium cycle and leading to a persistent efflux of $Ca^{2+}$ from the ER (Leal et al., 2015). Therefore, agents that inhibit $Ca^{2+}$ efflux from the ER can help restore calcium homeostasis and ultimately prolong neuronal survival.

Huntington's disease is a genetic disorder caused by a single mutation: the expansion of the CAG (poly-glutamine) repeat in the Huntington (Htt) gene. The disease targets medium spiny neurons in the striatum leading to characteristic motor impairment (Bezprozvanny, 2010). The mutant Huntington protein has been shown to elevate intracellular calcium in multiple ways, including by increasing the release from the ER (Bezprozvanny, 2010). Thus, treatments that reduce or inhibit calcium release from the ER could be beneficial in treating or managing the symptoms of HD, particularly motor dysfunction.

Spinocerebellar ataxias (SCA) are autosomal dominate genetic disorders caused by the expansion of the polyglutamine sequence in ataxin proteins (Atx) (Bezprozvanny, 2010). Each of the SCAs lead to degeneration of Purkinje cells in the cerebellum by targeting various components of the calcium homeostasis pathway. Interestingly, treating a mouse model of SCA with a RyR inhibitor and dantrolene (a $Ca^{2+}$ stabilizer) ameliorated the age dependent deficit of motor coordination in these mice and prevented the loss of neurons in the substantia nigra and the pontine nuclei (Chen et al., 2008). Thus, treatments that similarly target the RyR transporter or otherwise mitigate the loss of $Ca^{2+}$ from the ER could be useful to reduce SCA symptoms, particularly motor dysfunction.

Prion diseases include many spongiform encephalopathies such as Creutzfeldt Jacob's disease, kuru, familial insomnia, scrapie, and mad cow disease in animals. They are caused by the transmission of a misfolded prion protein ($PrP^{SC}$) into neuronal cells where it can associate with its native protein ($PrP^{C}$), trigger its misfolding and subsequent accumulation (Doyle et al., 2011). The end result is a progressively worsening disease characterized by widespread neurodegeneration (after death, infected brains appear riddled with holes). Altered ER $Ca^{2+}$ homeostasis and subsequent ER stress has been implicated in the pathogenesis in these diseases. The mutated $PrP^{SC}$ protein contains an apoptosis triggering domain that triggers the release of intracellular calcium stores. It also appears to upregulate ER $Ca^{2+}$ channels such as reticulon-3. In mice models, inhibition of ryanodine receptors (RyR) and inositol triphosphate receptors in the ER attenuated mitochondrial disruption and cell death (Doyle et al., 2011 and Ferreiro et al., Neurobiology of Disease 2008, 30:331-342). Therefore, therapies that similarly target calcium release from the ER can be useful to prevent the neuronal death associated with these diseases.

A therapeutically effective amount of at least one compound selected from the group consisting of JTV519, oxidized JTV519, salts and esters thereof, and mixtures thereof is administered in accordance with various methods of the present invention. A "therapeutically effective amount" refers to that amount of active ingredient which provides the desired result. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

In various embodiments, the compound (e.g., JTV519 and/or oxidized JTV519) is administered in an amount of from about 0.05 mg to about 100 mg, 0.05 mg to about 75 mg, 0.05 mg to about 50 mg, 0.05 mg to about 25 mg, from about 0.1 mg to about 100 mg, from about 0.1 mg to about 75 mg, from about 0.1 mg to about 50 mg, from about 0.1 mg to about 25 mg, or from about 1 mg to about 25 mg per kg of body weight depending upon the route of administration.

The pharmaceutical composition can be administered to the subject alone or in combination with at least one other active agent. In various embodiments, at least one additional active agent is administered in combination with JTV519 and/or oxidized JTV519. As such, aspects of the present invention are also directed to pharmaceutical compositions comprising a therapeutically effective amount of at least one compound selected from the group consisting of JTV519, oxidized JTV519, salts and esters thereof, and mixtures thereof and at least one additional active agent.

In some embodiments, the additional active agent comprises dantrolene, azumolene, or pharmaceutically acceptable salts or hydrates thereof "Dantrolene" as used herein refers to 1-[[5-(4-nitrophenyl)-2-furyl]methylideneamino]imidazolidine-2,4-dione or a pharmaceutically acceptable salt or hydrate thereof. One form of dantrolene is the monosodium salt of dantrolene or a hydrate thereof. Dantrolene sodium, a ryanodine receptor inhibitor, has been in clinical use since the 1980s for treating muscle dysfunction associated with malignant hyperthermia (MH). More recently, it has been used for the management of neuroleptic malignant syndrome, spasticity, heat stroke, and methamphetamine intoxication. WO2016/077706 A1, which is hereby incorporated herein by reference, describes the use of dantrolene for treating Wolfram syndrome and other ER stress disorders. Dantrolene is thought to depress excitation-contraction coupling in skeletal muscle by inhibiting the release of calcium ($Ca^{2+}$) from the sarcoplasmic reticulum, (smooth ER found in muscle cells). The molecular structure of dantrolene sodium is shown below.

Dantrolene sodium for injection is commercially available as DANTRIUM INTRAVENOUS (JHP Pharmaceuticals, Parsippany, N.J.). It is a sterile, non-pyrogenic, lyophilized formulation supplied in 70 mL vials containing 20 mg dantrolene sodium, 3000 mg mannitol, and sufficient sodium hydroxide to yield pH of approximately 9.5 when reconstituted with 60 mL sterile water for injection USP. Dantrolene sodium capsules are commercially as DANTRIUM (JHP Pharmaceuticals, Parsippany, N.J.). DANTRIUM is supplied in capsules of 25 mg, 50 mg, and 100 mg.

Dantrolene is highly lipophilic and poorly soluble in water. A more water soluble analog of dantrolene called azumolene is under development for similar indications as dantrolene. Azumolene, has a bromine group instead of the p-nitro group found in dantrolene, and is thirty times more water soluble. "Azumolene" as used herein refers to 1-[[5-(4-bromophenyl)-2-furyl]methylideneamino]imidazolidine-2,4-dione or a pharmaceutically acceptable salt or hydrate thereof. Thus, another additional active agent useful in the methods of the present invention includes azumolene.

In further embodiments, the additional active agent comprises a glitazone. Glitazones include, for example, pioglitazone, rosiglitazone, lobeglitazone. In certain embodiments, the additional active agent comprises GLP-1. In some embodiments, thee additional active agent comprises sitagliptin. In various embodiments, the additional active agent comprises metformin.

The term "combination" designates a treatment wherein at least two or more drugs are co-administered to a subject to cause a biological effect. In combination therapy, the at least two actives (e.g., JTV519 and dantrolene) may be administered together or separately, at the same time or sequentially. Also, the at least two active agents may be administered through different routes and protocols. As a result, although they may be formulated together, the active agents of a combination may also be formulated separately.

The pharmaceutical composition can be administered by routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. In certain embodiments, the pharmaceutical composition is administered parenterally (e.g., intravenously) to the subject. In some embodiments, the pharmaceutical composition is administered orally to the subject.

In addition to the compound (e.g., JTV519 and/or oxidized JTV519), the pharmaceutical composition can contain one or more excipients. Pharmaceutically acceptable excipients for use in the compositions of the present invention are selected based upon a number of factors including the particular compound used, and its concentration, stability and intended bioavailability; the disease, disorder or condition being treated with the composition; the subject, its age, size and general condition; and the route of administration.

A pharmaceutical composition for oral administration can be formulated using pharmaceutically acceptable excipients known in the art suitable for oral administration. Such excipients enable the pharmaceutical compositions to be formulated as tablets, pills, dragees, capsules, liquids, gels, syrups, slurries, suspensions, and the like, for ingestion by the subject. Suitable excipients for oral dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, microcrystalline cellulose, colloidal silicon dioxide, croscarmellose sodium, talc, magnesium stearate, and stearic acid. Further, such oral dosage forms can be uncoated or can be coated to delay disintegration and absorption.

In certain embodiments, the composition is formulated for parenteral administration. Dosage forms suitable for parenteral administration include solutions, suspensions, dispersions, emulsions or any other dosage form that can be administered parenterally.

Further details on techniques for formulation and administration can be found in the latest edition of REMINGTON'S PHARMACEUTICAL SCIENCES (Mack Publishing Co., Easton, Pa.). Pharmaceutically acceptable excipients are also identified, for example, in *The Handbook of Pharmaceutical Excipients*, (American Pharmaceutical Association, Washington, D.C., and The Pharmaceutical Society of Great Britain, London, England, 1968). Additional excipients can be included in the pharmaceutical compositions of the invention for a variety of purposes.

These excipients can impart properties which enhance retention of the compound at the site of administration, protect the stability of the composition, control the pH, facilitate processing of the compound into pharmaceutical compositions, and so on. Other excipients include, for example, fillers or diluents, surface active, wetting or emulsifying agents, preservatives, agents for adjusting pH or buffering agents, thickeners, colorants, dyes, flow aids, non-volatile silicones, adhesives, bulking agents, flavorings, sweeteners, adsorbents, binders, disintegrating agents, lubricants, coating agents, and antioxidants.

"Pharmaceutically acceptable salt" as used herein refers to salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, alkyl having from 1 to 6 carbon atoms, sulfonate, and aryl sulfonate.

"Subject" as used herein refers to an animal, including both human and non-human mammals. Subjects include veterinary subjects, including livestock such as cows and sheep, rodents (such as mice and rats), and non-human primates. Preferred subjects are human subjects.

EXAMPLES

The following non-limiting examples are provided to further illustrate the present invention.

Example 1

Materials and Methods

Thapsigargin was obtained from Sigma-Aldrich (St. Louis, Mo.). Growth media RPMI-1640 and Dulbecco's Modified Eagle Medium (DMEM) were obtained from Invitrogen (Carlsbad, Calif.). Fluo-4 and Fura-2AM calcium indicators were obtained from INVITROGEN (Carlsbad, Calif.). Caspase-glo 3/7 protease assay kit and calpain-glo protease assay kit were obtained from Promega (Madison, Wis.).

Cell Culture

HEK293 cells were cultured in DMEM containing 10% FBS and penicillin and streptomycin (ThermoFisher Scientific, Waltham, Mass.). INS-1 832/13 cells were cultured in RPMI containing 10% FBS before measurement.

Caspase 3/7 Activity Assay

A Caspase 3/7 assay (Promega, Madison, Wis.) was utilized to measure caspase-3 and -7 activities in various cell lines. The assay provides a proluminescent caspase-3/7 substrate, which contains the tetrapeptide sequence DEVD. This caspase-3/7 substrate can be added directly to cell lysates. The substrate is cleaved to release an aminoluciferin, which is a substrate for luciferase used in the production of light. The signal is proportional to caspase-3/7 activity. The stabilized luciferase and proprietary buffer system improve assay performance across a wide range of assay conditions, and the assay is less likely to be affected by compound interference unlike fluorescent- or colorimetric-based assays Statistical Analysis Two-tailed t-tests were used to compare data. P values below 0.05 were considered significant. All values are shown as means±s.d. if not stated.

Example 2

ER Calcium-Depletion in Wolfram Syndrome

Figure 2:
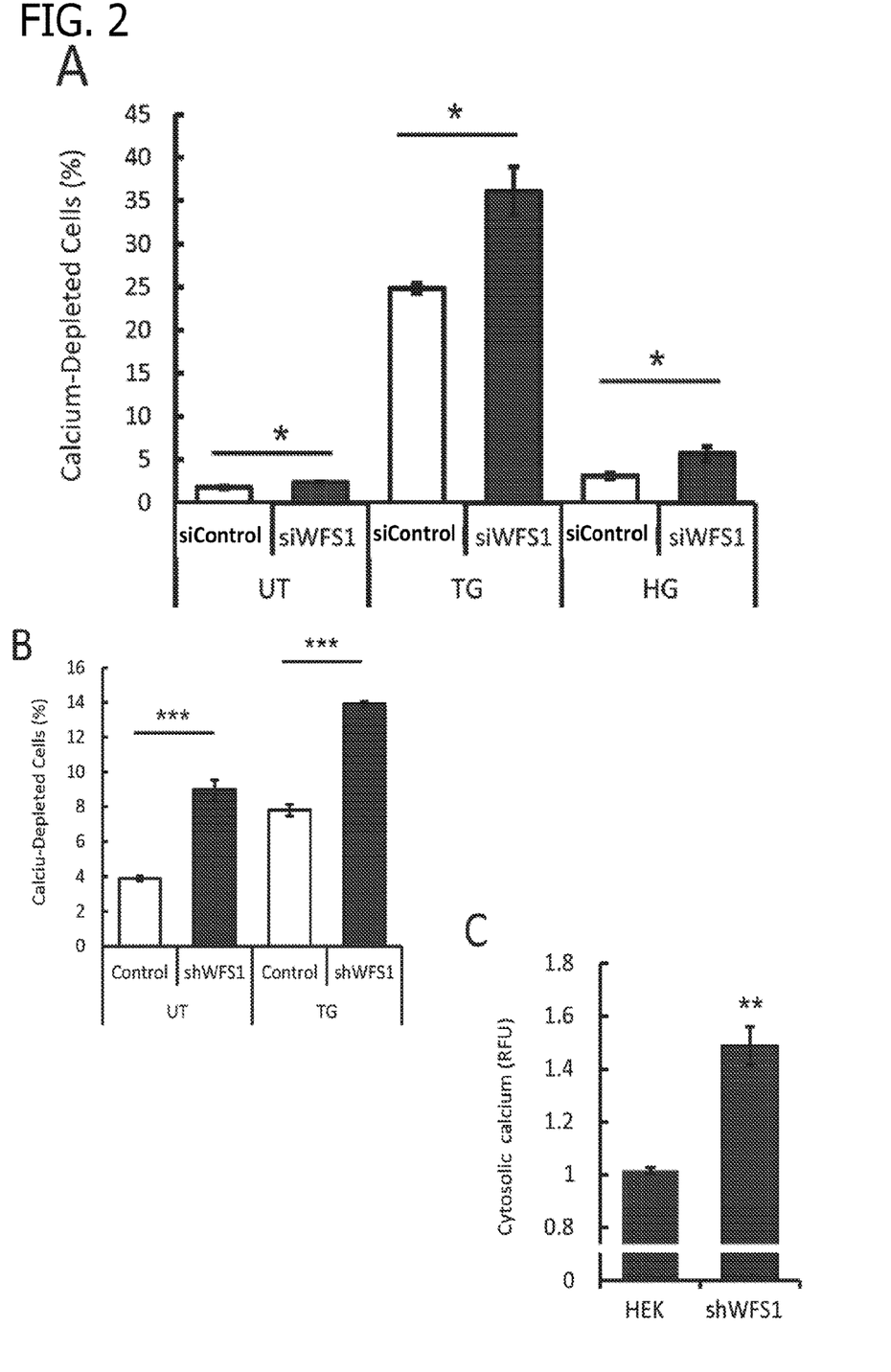
FIG. 2 depicts (A) rates of ER calcium-depleted INS-1 832/13 cells transfected with control scramble siRNA or siRNA directed against WFS1, and then untreated or treated with 10 nM thapsigargin (TG) for 24 h or 25 mM high glucose (HG, 25 mM) for 48 h; (B) rates of ER calcium-depleted HEK293 cells transduced with lentivirus expressing control scramble shRNA or shRNA directed against WFS1, and then untreated or treated with 10 nM thapsigargin (TG) for 24 h; and (C) cytosolic calcium levels of HEK293 cells transduced with lentivirus expressing control scramble shRNA or shRNA directed against WFS1.

INS-1 832/13 cells transfected with scrambled siRNA or siRNA directed against WFS1 were treated with 10 nM thapsigargin for 24 hours or 25 mM high glucose for 48 hours. The percent rates of ER calcium depletion in INS-823/13 cells stained with Fluro-4 are shown in FIG. 2, A. RNAi-mediated knockdown of WFS1 in INS-1 832/13 cells increased the rate of ER-calcium depleted cells under ER stress or high glucose conditions.

(B) Rates of ER calcium-depleted HEK293 cells transduced with lentivirus expressing control scramble shRNA or shRNA directed against WFS1, and then untreated or treated with 10 nM thapsigargin (TG) for 24 h. (C).

HEK293 cells were transfected with lentivirus expressing scrambled shRNA or shRNA directed against WFS1 and then treated with 10 nM thapsigargin for 24 hours. shRNA-mediated knockdown of WFS1 in HEK293 cells, stained with Fluo-4, also increased the rate of ER calcium-depleted cells under normal and ER stress conditions (FIG. 2, B).

Cytosolic calcium levels of HEK293 cells were transduced with lentivirus expressing control scramble shRNA or shRNA directed against WFS1 and then untreated or treated with 10 nM thapsigargin for 24 h. Calcium levels were determined by Fluo-4 AM (FIG. 2, C). Collectively, these results indicate that loss of function of WFS1 increases cytoplasmic calcium levels, leading to calpain activation.

Example 3

Targeting ER Calcium Homeostasis

Figure 3:
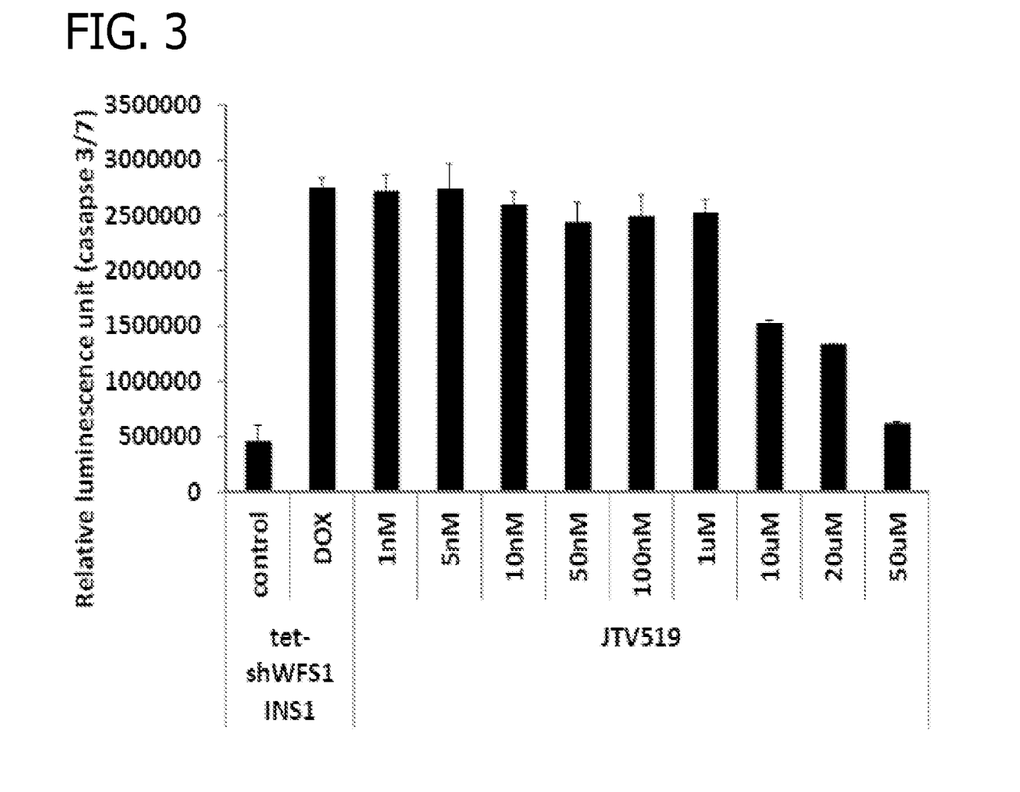
FIG. 3 is a graph illustrating suppression of cell death in WFS1 depleted INS-1 832/13 cells with JTV519.
Figure 4:
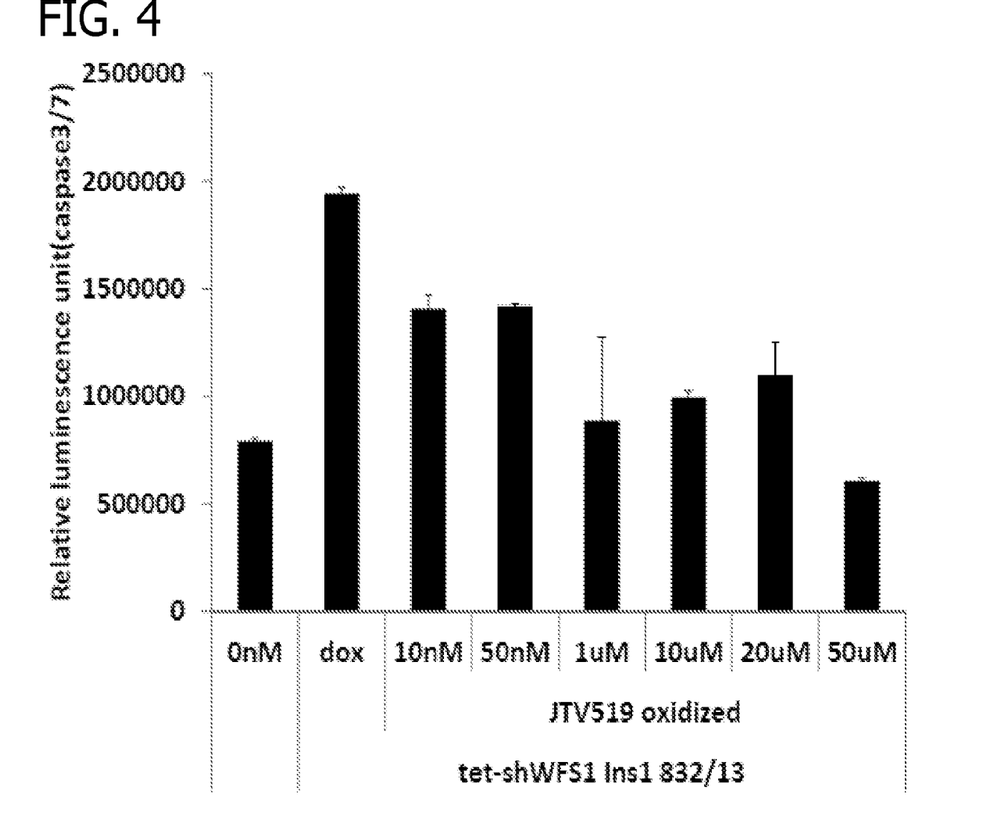
FIG. 4 is a graph illustrating suppression of cell death in WFS1 depleted INS-1 832/13 cells with oxidized JTV519.

INS-1 832/13 cells in which WFS1 expression could be depleted by doxycycline (DOX)-inducible expression of shWFS1 were pretreated with or without various concentrations of JTV519 or oxidized JTV519 for 24 h and then treated with DOX for 48 h to deplete WFS1 and induce cell death. Apoptosis was measured by monitoring Caspase 3/7 activation. FIGS. 3 and 4 show that JTV519 and oxidized JTV519 (also referred to JTV519-oxidized), respectively, suppress cell death in WFS1 depleted INS-1 832/13 cells.

Example 4

Decreasing Cytosolic Calcium Levels in INS-1832/13 Cells

Figure 5:
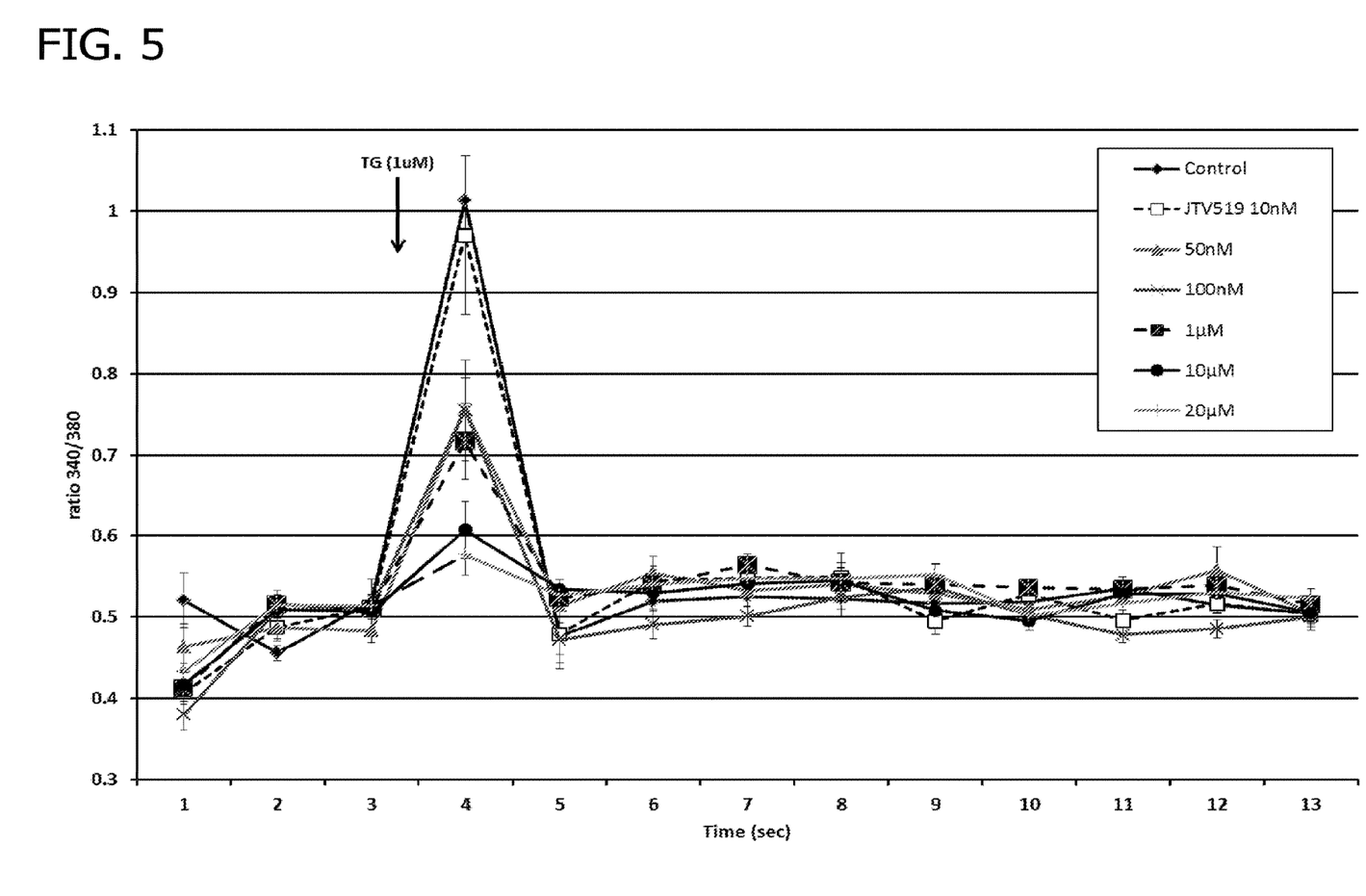
FIG. 5 is a graph illustrating decreased cytosolic calcium levels in INS-1 832/13 cells treated with JTV519 and challenged with thapsigargin.
Figure 6:
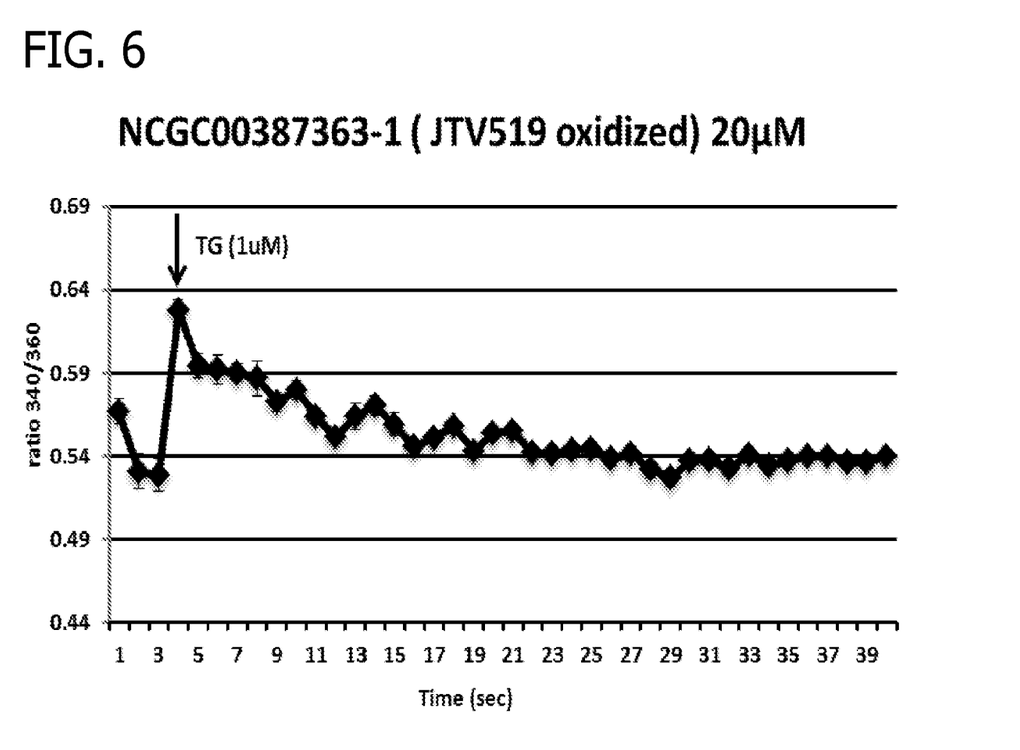
FIG. 6 is a graph illustrating decreased cytosolic calcium levels in INS-1 832/13 cells treated with oxidized JTV519 and challenged with thapsigargin.

INS-1 832/13 cells were treated with JTV519 or JTV519-oxidized over a range of concentrations. Cytoplasmic calcium levels were measured by Fura-2AM calcium indicator over a period of minutes. Thapsigargin (1 µM) was added at the time point indicated by an arrow (n=6, the experiment was repeated 6 independent times) on FIGS. 5 and 6. The results show that both JTV519 and JTV519-oxidized decreased cytosolic calcium levels in INS-1 832/13 cells. See FIGS. 5 and 6.

Example 5

Protection from Thapsigargin-Mediated Cell Death in INS-1 832/13 Cells

Figure 7:
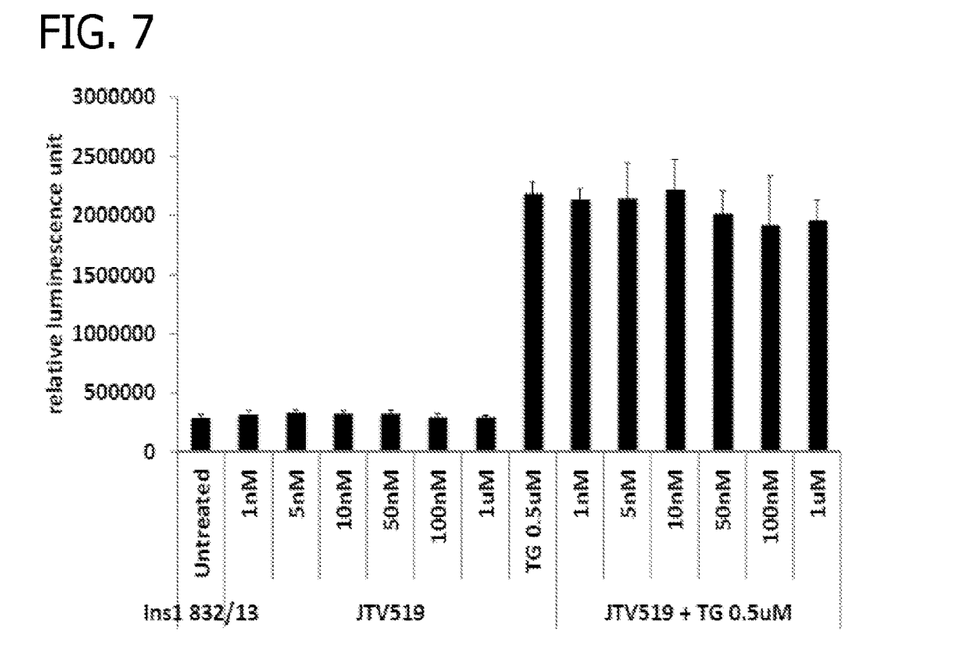
FIG. 7 is a graph illustrating cell death in INS-1 823/13 cells treated with JTV519 and challenged with thapsigargin.
Figure 8:
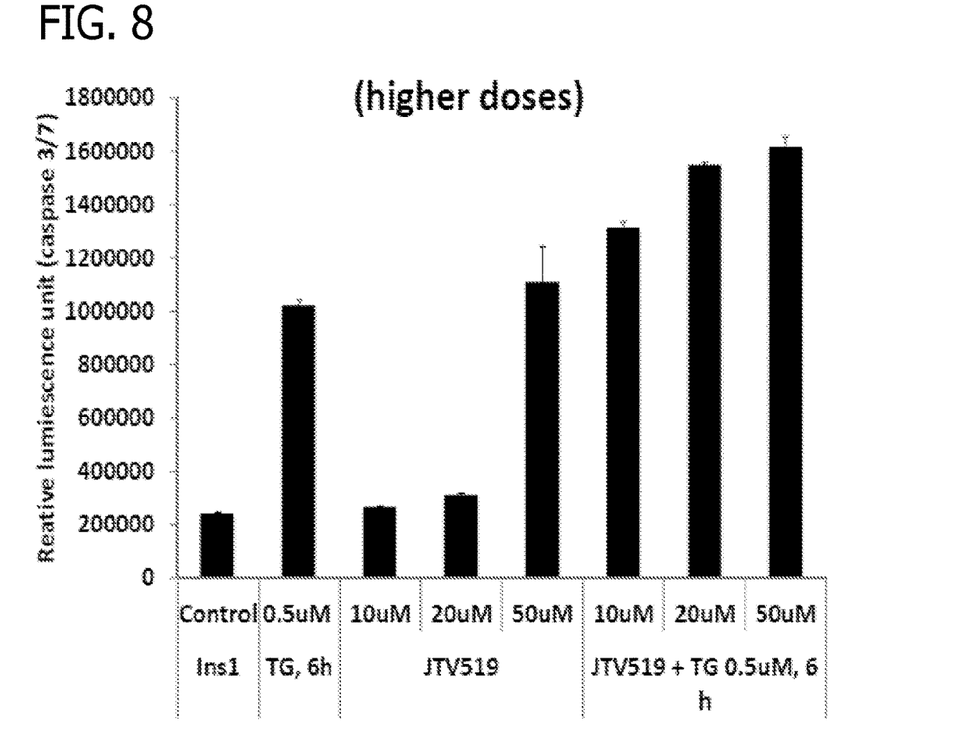
FIG. 8 is a graph illustrating cell death in INS-1 823/13 cells treated with JTV519 and challenged with thapsigargin.
Figure 9:
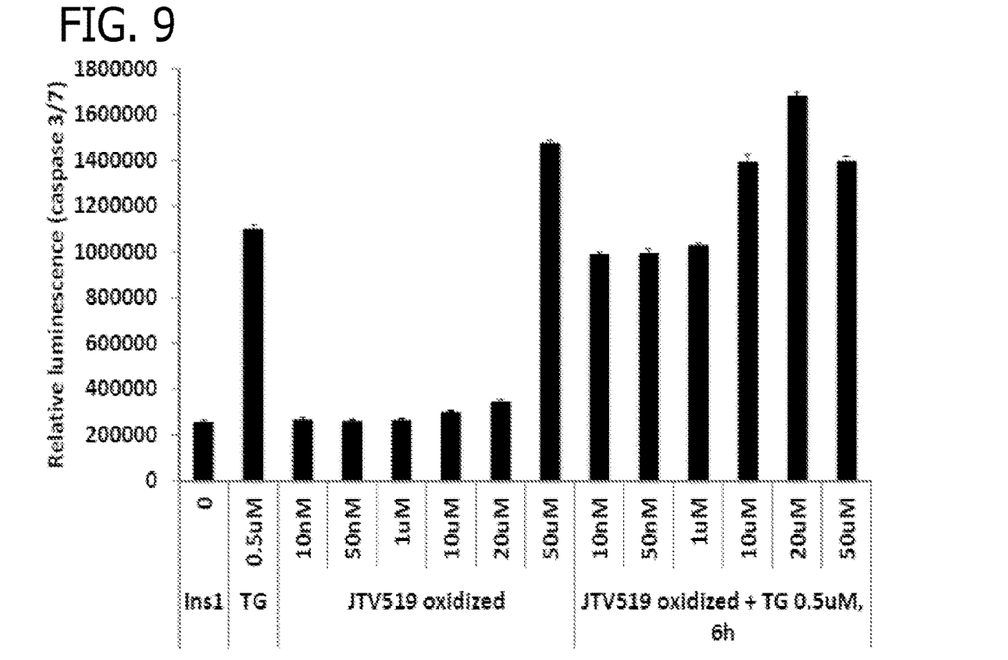
FIG. 9 is a graph illustrating cell death in INS-1E cells treated with oxidized JTV519 and challenged with thapsigargin.

The pathway leading to calpain-2 activation provides potential therapeutic targets for Wolfram syndrome, such as leakage of ER calcium to the cytosol. To test this concept, a small-scale screen was performed to identify chemical compounds that could prevent cell death mediated by thapsigargin, a known inhibitor for ER calcium ATPase. INS-1 823/13 cells were pretreated with 24 hours the incubated in media containing 0.5 nM of thapsigargin (TG) overnight. Apoptosis was detected by caspase 3/7-Glo luminescence. FIGS. 7 and 8 show that JTV519 did not significantly suppress thapsigargin mediated cell death. However, as shown in FIG. 9, JTV519-oxidized suppressed thapsigargin-mediated cell death.

Example 6

Protection of INS-1E Cells from Cytokine-Induced Cell Death

Figure 10:
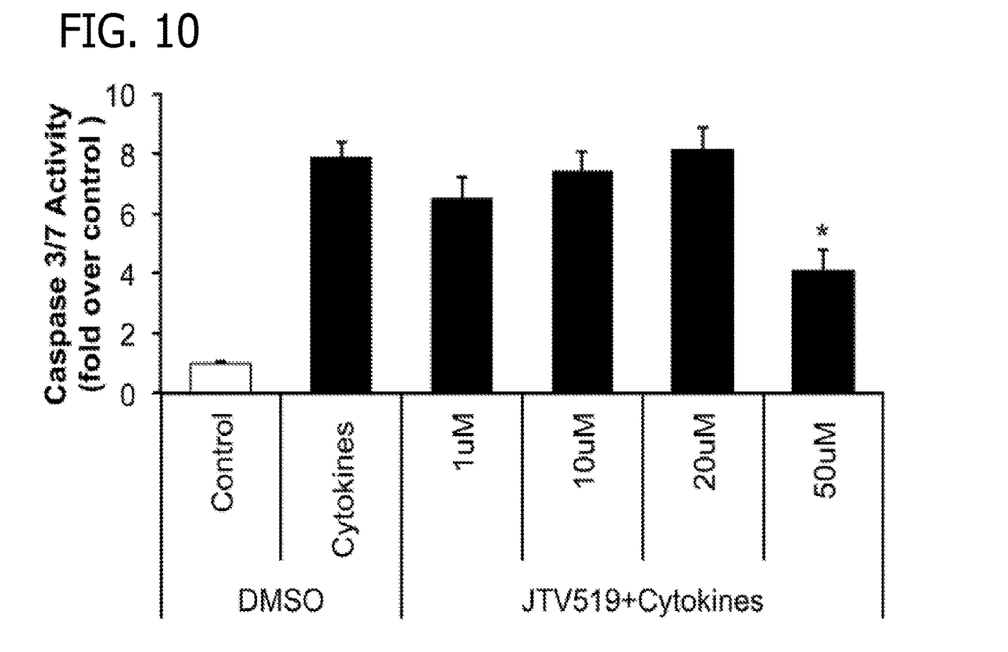
FIG. 10 is a graph illustrating protection of INS-1E cells from cytokine-induced cell death with JTV519.

To determine whether JTV519 can prevent ER calcium depletion and confer protection against ER stress-mediated cell death in a cell model of type 1 diabetes. INS-1E cells were pre-treated with 1 µM-50 µM of JTV519 for 24 hours then stressed for 24 hours with cytokines (IL-1β and IFN-γ 50 ng/ml). Apoptotic cell death was measured via caspase 3/7 activity assay. The data presented in FIG. 10 shows that JTV519 protects INS-1E cells from cytokine-induced cell death. Data are expressed as mean±SEM from three independent experiments. *p<0.05 compared to cytokine treated cells unpaired t-test.

Example 7

Pharmacokinetic Study of JTV519

To study the pharmacokinetics of JTV519, the compound was synthesized as the HCl salt and formulated as a clear solution in 20% HP-β-CD in saline and intraperitoneally injected into CD1 mice. Samples of blood and pancreas tissue and whole brain and heart organs were collected from the mice and analyzed.

An ultra-performance liquid chromatography-tandem mass spectrometry (UPLC-MS/MS) method was developed to determine sample concentrations in the samples. Mass spectrometric analysis was performed on a Waters Xevo TQ-S triple quadrupole instrument using electrospray ionization in positive mode with the selected reaction monitoring (SRM). The MS/MS parameters were optimized by infusion compounds. The separation was performed on an Acquity BEH C18 column (50×2.1 mm, 1.7µ) using a Waters Acquity UPLC system with 0.6 mL/min flow rate and gradient elution. The column temperature was maintained at 60° C. The calibration standards (1.0-5000 ng/mL) and quality control samples were prepared in the blank mouse plasma. 10 µL plasma samples were mixed with 200 µL internal standard in acetonitrile to precipitate proteins in a 96-well plate. 1.0 µL supernatant was injected for the UPLC-MS/MS analysis The results of the pharmacokinetic study are presented in Table 1. The results show that JTV519 had good solubility and permeability and passed the blood brain barrier.

TABLE 1

| Admin. Dosage of JTV519 | Sample | Cmax (µg/mL) | $t_{1/2}$ (h) | $AUC_{0-\infty}$ (h * µg/mL) | AUC ratio (with plasma) |
|---|---|---|---|---|---|
| ip (30 mg/kg) | plasma | 1.81 | 7.1 | 3.46 | |
| ip (30 mg/kg)$^a$ | brain | 5.13 | 5.1 | 10.1 | 2.9 |
| ip (30 mg/kg)$^a$ | heart | 14.3 | 4.0 | 29.2 | 8.4 |
| ip (30 mg/kg)$^a$ | pancreas | 105 | 4.5 | 146 | 42 |

$^a$n = 3 (CD-1 mouse).

Example 8

Motor Function Study

WFS1 gene knockout mice, a mouse model of Wolfram syndrome, were treated with JTV519 (i.p. injections, 15 mg/kg/day, 5 days per week) or saline after they become 6 weeks old for 6 weeks (5 female mice for each group). Littermate wild-type control mice were treated by saline (VEH) for 6 weeks (3 female mice). Motor functions of the WFS1 knockout were evaluated using a 90° inclined screen test.

For the 90° inclined screen test, each mouse was placed on top of an elevated (47 cm above the floor) wire mesh grid (16 squares per 10 cm) that was inclined to 90°. Each mouse was placed in the middle of the screen with its head oriented down and was timed for how long it remained on the screen and how long it took to climb to the top of the screen. A maximum score of 60 s was given if an animal did not fall.

Figure 11:
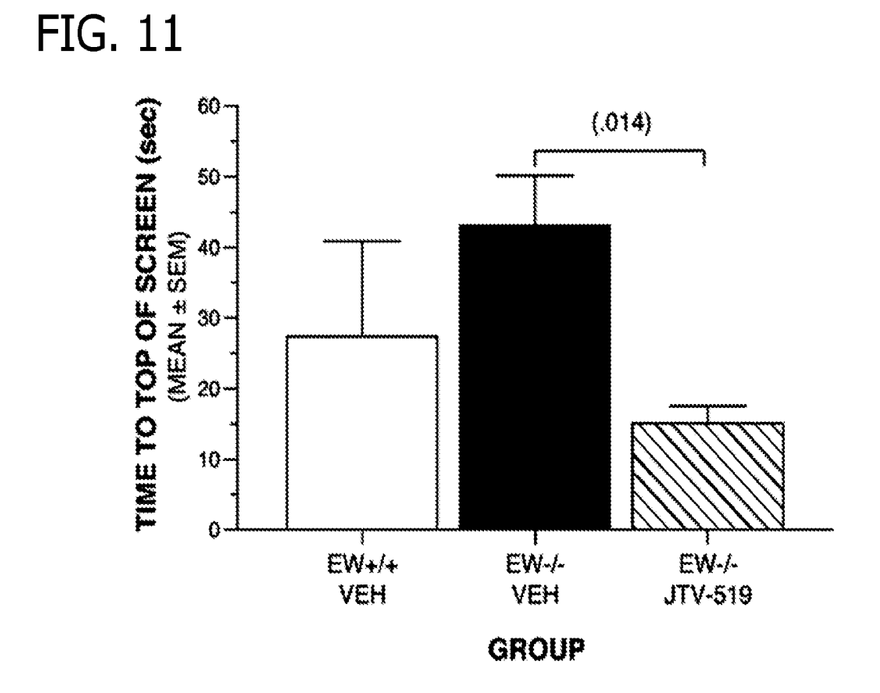
FIG. 11 is a graph illustrating the results of a motor function test with WFS1 mice administered with JTV519.

The results of this test are provided in FIG. 11. The mice administered JTV519 exhibited improved motor functions as indicated by a significantly reduced amount of time to reach the top of the screen as compared to the control mice (significant group effect: p=0.41).

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

Having described the invention in detail, it will be apparent that modifications and variations are possible without departing from the scope of the invention defined in the appended claims.

What is claimed is:

1. A method for treating or preventing Wolfram syndrome in a subject in need thereof comprising administering to the subject a pharmaceutical composition comprising a therapeutically effective amount of at least one compound selected from the group consisting of JTV519, oxidized JTV519, salts and esters thereof, and mixtures thereof.

2. The method of claim 1, wherein the compound is administered in an amount of from about 0.05 mg to about 100 mg per kg of body weight.

3. The method of claim 1, wherein the pharmaceutical composition is administered parenterally to the subject.

4. The method of claim 1, wherein the pharmaceutical composition is administered orally to the subject.

5. The method of claim 1, further comprising administering at least one additional active agent to the subject.

6. The method of claim 5, wherein the additional active agent comprises dantrolene, azumolene, or pharmaceutically acceptable salts or hydrates thereof.

7. The method of claim 5 wherein the additional active agent comprises a glitazone, GLP-1, sitagliptin, and/or metformin.

8. The method of claim 1, wherein the subject is a human.

9. The method of claim 1, wherein the method treats clinical symptoms of Wolfram syndrome.

10. The method of claim 9, wherein the clinical symptoms comprise β cell and neuronal cell death.

11. The method of claim 5 wherein the additional active agent comprises sitagliptin and/or metformin.

* * * * *